United States Patent [19]

Licke

[11] 4,070,391

[45] Jan. 24, 1978

[54] PROCESS FOR PRODUCING ISOCYANATE FROM NITRO COMPOUNDS AND CARBON MONOXIDE USING RHODIUM OXIDE CATALYSTS

[75] Inventor: George C. Licke, Deer River, Minn.

[73] Assignee: Ethyl Corporation, Richmond, Va.

[21] Appl. No.: 726,642

[22] Filed: Sept. 27, 1976

Related U.S. Application Data

[63] Continuation-in-part of Ser. No. 615,763, Sept. 22, 1975, abandoned.

[51] Int. Cl.² .......................................... C07C 118/06
[52] U.S. Cl. .......................... 260/453 PC; 252/430; 252/472; 260/397.6
[58] Field of Search .................................. 260/453 PC

[56] References Cited

U.S. PATENT DOCUMENTS

| 3,576,836 | 4/1971 | Prichard | 260/453 PC |
| 3,728,370 | 4/1973 | Ottmann et al. | 260/453 PC |

FOREIGN PATENT DOCUMENTS

1,025,436  4/1966  United Kingdom.

*Primary Examiner*—Dolph H. Torrence
*Attorney, Agent, or Firm*—Donald L. Johnson; Robert A. Linn; Willard G. Montgomery

[57] ABSTRACT

In the process for preparing isocyanate, particularly aromatic isocyanate, by the reaction of an organic nitro compound, particularly an aromatic dinitro compound with carbon monoxide in the presence of a catalyst, the improvement which comprises employing as said catalyst rhodium oxide, particularly substantially amorphous rhodium oxide, and conducting the reaction in the presence of a promoter quantity of a nitrilic solvent, such as acetonitrile.

15 Claims, No Drawings

PROCESS FOR PRODUCING ISOCYANATE FROM NITRO COMPOUNDS AND CARBON MONOXIDE USING RHODIUM OXIDE CATALYSTS

CROSS-REFERENCE TO RELATED APPLICATIONS

This application is a continuation-in-part of copending application Ser. No. 615,763, filed Sept. 22, 1975, now abandoned.

BACKGROUND OF THE INVENTION

It is known in the art to manufacture organic isocyanates by reacting organic nitro compounds with carbon monoxide in the presence of a catalyst in a liquid phase.

British Pat. No. 1,025,436 discloses a process for preparing isocyanates from the corresponding nitro compounds by reacting an aromatic nitro compound with carbon monoxide in the presence of a noble metal based catalyst in a liquid phase. It has been reported, however, that this process is not used commercially because no more than trace amounts of aromatic isocyanates are formed when an aromatic nitro compound such as dinitrotoluene is reacted with carbon monoxide using a noble metal based catalyst such as rhodium trichloride, palladium trichloride, iridium trichloride, osmium chloride and the like.

For years, attempts have been made to find more efficient methods for producing organic isocyanates by the catalyzed carbonylation of nitro compounds at elevated temperatures and pressures. For example, U.S. Pat. No. 3,576,836 to Prichard teaches a process for preparing aromatic isocyanates by carbonylation, at elevated temperatures and pressures, of aromatic mono- or dinitro compounds in the presence of a palladous halide and an organic cyano compound. U.S. Pat. No. 3,728,370 to Ottman et al. teaches a process for providing organic isocyanate by reacting an organic nitro compound with carbon monoxide in the presence of a noble metal based catalyst and an unsaturated organic compound having at least one multiple bond conjugated to another multiple bond in selected aliphatic or cycloaliphatic systems or in the presence of an unsaturated organic compound having at least one multiple bond conjugated to an aromatic hydrocarbon nucleus.

Other catalysts taught in the prior art are a mixture of a noble metal based catalyst and a non-noble based catalyst, U.S. Pat. No. 3,523,966 to Ottman et al.; a mixture of a noble metal based compound and an organophosphorus compound, U.S. Pat. No. 3,523,962 to Kober et al.; a mixture of (a) an inorganic copper compound, (b) at least one compound selected from the group consisting of elemental palladium, elemental rhodium, palladium halides, rhodium halides, palladium oxides and rhodium oxides, and (c) at least one oxide of an element selected from the group consisting of vanadium, molybdenum, tungsten, niobium, chromium and tantalum.

Further, U.S. Pat. No. 3,754,014 to Kober et al. discloses carrying out the carbonylation process in the vapor phase in the presence of a noble metal based catalyst and preferably utilizing a halide of copper as a catalyst component.

Quite surprisingly, it has now been discovered that high yields of aromatic isocyanates and diisocyanates can be derived from aromatic nitro compounds simply by reacting an aromatic dinitro compound with carbon monoxide at an elevated temperature and an elevated pressure in the presence of a rhodium oxide catalyst and an organic nitrile compound.

SUMMARY OF THE INVENTION

Conversion of organic nitro compounds to isocyanate is obtained by reacting a nitro compound, particularly a dinitro compound, with carbon monoxide in the presence of an amorphous rhodium oxide catalyst, specifically rhodium dioxide or rhodium sesquioxide, and a promoter quantity of a nitrilic solvent, particularly acetonitrile.

DESCRIPTION OF THE PREFERRED EMBODIMENTS

The present invention is embodied in a method for producing isocyanates, particularly aromatic isocyanates, from an organic nitro, particularly aromatic nitro, compound. In the process of the present invention an organic nitro compound is reacted with carbon monoxide in the presence of a rhodium oxide catalyst and a promoter amount of a solvent comprised of an organic nitrile compound, to produce isocyanate.

The organic nitro compounds for use in the process of the present invention can be aliphatic or aromatic nitro compounds. The aliphatic and aromatic nitro compounds can be substituted or unsubstituted. When substituted, they can be substituted with one or more substituents such as nitroalkyl, alkyl, alkenyl, alkoxy, aryloxy, halogen, alkylthio, arylthio, carboxyalkyl, and the like. Preferred nitro compounds contain up to about 20 carbon atoms; more preferred nitro compounds contain up to 16 carbon atoms. Most preferred nitro compounds contain up to 10 carbon atoms. Some general examples of suitable aromatic nitro compounds are mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, tolyl, xylyl, naphthyl, chlorophenyl, chlorotolyl, chloroxylyl or chloronaphthyl, chloronitrobenzenes, dinitro compounds such as dinitrobenzene, alkyl and alkoxy dinitrobenzenes wherein the alkyl group contains up to 10 carbon atoms, aryl and aryloxy dinitrobenzenes wherein the aryl group is phenyl, tolyl, xylyl, naphthyl, chlorophenyl, chlorotolyl, chloroxylyl or chloronaphthyl, chlorodinitrobenzenes, trinitro compounds such as trinitrobenzene, alkyl and alkoxytrinitrobenzenes, aryl and aryloxytrinitrobenzenes, wherein the aryl group is phenyl, tolyl, xylyl, naphthyl, chlorophenyl, chlorotolyl, chloroxylyl or chloronaphthyl, and chlorotrinitrobenzenes as well as similarly substituted mono- and polynitro derivatives of the naphthalene, diphenyl, diphenylmethane, anthracene and phenanthrene series. Some specific examples of suitable substituted aromatic nitro compounds are: o-nitrotoluene, m-nitrotoluene, p-nitrotoluene, o-nitro-p-xylene, 2-methyl-1-nitronaphthalene, m-dinitrobenzene, p-dinitrobenzene, 2,4-dinitrotoluene, 2,6-dinitrotoluene, dinitromesitylene, 4,4'-dinitrobiphenyl, 2,4-dinitrobiphenyl, 4,4'-dinitrobibenzyl, bis-(p-nitrophenyl)ether, bis(2,4-dinitrophenyl)ether, bis(p-nitrophenyl)thioether, bis(p-nitrophenyl) sulfone, α,α'-dinitro-p-xylene, 2,4,6-trinitrotoluene, 1,3,5-trinitrobenzene, 1-chloro-2-nitrobenzene, 1-chloro-4-nitrobenzene, 1-chloro-3-nitrobenzene, 2-chloro-6-nitrotoluene, 4-chloro-3-nitrotoluene, 1-chloro-2,4-dinitrobenzene, 1,4-dichloro-2-nitrobenzene, α-chloro-p-nitrotoluene, 1,3,5- trichloro-2-nitrobenzene, 1,3,5-trichloro-2,4-dinitrobenzene, 1,2-dichloro-4-nitrobenzene, α-chloro-m-nitrotoluene, 1,2,4-trichloro-5-nitrobenzene, 1-bromo-4-nitrobenzene, 1-bromo-2-nitrobenzene, 1-bromo-3-nitrobenzene, 1-bromo-2,4-dinitrobenzene, α,α-dibromo-p-nitrotoluene, α-bromo-p-nitrotoluene, 1-fluoro-4-nitrobenzene, 1-fluoro-2,4-dinitrobenzene, 1-fluoro-2-nitrobenzene, o-nitroanisole, p-nitroanisole, p-nitrophenetole, o-nitrophenetole, 2,4-dinitrophenetole, 2,4-dinitroanisole, 1-chloro-2,4-dimethoxy-5-nitrobenzene, 1,4-dimethoxy-2-nitrobenzene, m-nitrobenzaldehyde, p-nitrobenzaldehyde, p-nitrobenzoylchloride, m-nitrobenzoylchloride, 3,5-dinitrobenzoylchloride, ethyl-p-nitrobenzoate, methyl-o-nitrobenzoate, m-nitrobenzenesulfonylchloride, p-nitrobenzenesulfonylchloride, o-nitrobenzenesulfonylchloride, 4-chloro-3-nitrobenzenesulfonylchloride, and 2,4-dinitrobenzenesulfonylchloride. Some typical examples of substituted or unsubstituted aliphatic nitro compounds are nitromethane, nitroethane, nitropropanes, nitrobutanes, nitrohexanes, nitrocyclopentane, nitrocyclohexane, nitrocyclobutane, nitrooctanes, nitrooctadecanes, 3-nitropropene-1, phenylnitromethane, p-bromophenylnitromethane, p-nitrophenylnitromethane, p-methoxyphenylnitromethane, dinitroethane, dinitropropane, dinitrobutane, dinitrohexane, dinitrodecane, dinitrocyclohexane, dinitromethylcyclohexane, and dinitrocyclohexylmethane. For the production of diisocyanates the dinitro compounds are preferred. The most preferred dinitro aromatic compounds are the dinitrobenzenes and dinitrotoluenes, particularly 2,4- and 2,6-dinitrotoluene.

The solvents which are employed in the process of this invention are the organic cyano compounds. These compounds may be aliphatic or aromatic cyano compounds. Preferred cyano compounds are those containing up to about 20 carbon atoms. More preferred cyano compounds are those containing up to about 16 carbon atoms. Most preferred cyano compounds are those containing up to 10 carbon atoms. Some examples of the organic nitrile compounds are acetonitrile, propionitrile, n-butyronitrile, isobutyronitrile, n-valeronitrile, benzonitrile, toluenitrile, and the like. Some examples of dinitriles are succininitrile, glutaronitrile, adiponitrile and the like. Mixtures of organic cyanides can be used in the present process. The preferred cyanides are the alkyl cyanides with the more preferred cyanides being the lower alkyl cyanides. The most preferred cyanide is acetonitrile.

The rhodium oxide catalyst employed can be $RhO_2$ or $Rh_2O_3$. The rhodium oxide catalyst should be amorphous rhodium oxide. By amorphous rhodium oxide is meant rhodium oxide which is substantially amorphous, that is, the greater part, by weight, of which is in an amorphous state. Small quantities of crystalline rhodium oxide may be present, as long as the proportion of crystalline rhodium oxide to amorphous rhodium oxide is not great enough so as to deleteriously affect the properties of the amorphous rhodium oxide as a catalyst.

Generally, the amorphous rhodium oxide which can be used is commercially available amorphous rhodium oxide, such as that produced by Pfaltz and Bauer, Inc. of Flushing, N.Y. It is not necessary to vigorously exclude crystalline rhodium oxide from the rhodium oxide insomuch as the amount of crystalline rhodium oxide present in the rhodium oxide is not detrimental to the improved process. Generally, the amount of crystalline rhodium oxide present should be less than 50 percent by weight, preferably less than 25 percent by weight, more preferably less than 10 percent by weight, and most preferably less than 1 percent by weight. That is to say, more preferably the rhodium oxide should be about 99 percent amorphous rhodium oxide.

The two oxides of rhodium which are used as catalysts are rhodium dioxide, $RhO_2$, and rhodium sesquioxide, $Rh_2O_3$, both of which are amorphous or substantially amorphous.

The discovery has been made that isocyanates can be prepared in high yields by the reaction of an organic nitro compound with carbon monoxide in the presence of a generally amorphous rhodium oxide catalyst and a promoter amount of a nitrilic solvent. That is to say, by the process of the present invention, compounds containing one or more isocyanate groups can be prepared; specifically, mixtures of mono- and diisocyanates are derivable from aromatic dinitro compounds according to the present process. The reaction is conducted under CO pressure. The CO pressures used may be subatmospheric pressures, atmospheric pressures or superatmospheric pressures. Superatmospheric pressures are preferred as at pressures above ambient, the reaction rate is generally increased. There is no real upper limit on the CO pressures that can be used and the upper limit is, therefore, determined by such secondary considerations as cost, equipment design, and the like. While, generally, the pressures can range from atmospheric pressure, provided enough CO can be present at atmospheric pressure to react with the nitro compound, to the aforementioned upper limit, a preferred range of pressures is from about 600 p.s.i. to about 10,000 p.s.i. A more preferred range of pressures is from about 1,000 p.s.i. to about 8,000 p.s.i., while a most preferred range of pressures is from about 1,500 p.s.i. to about 5,000 p.s.i. Generally the amount of CO required is an amount sufficient to coreact with the nitro compound to form isocyanate. For complete theoretical conversion of the nitro compound to the isocyanate at least 3 CO groups are required for every $NO_2$ group in the nitro compound. Therefore, generally 3 or more CO groups for every $NO_2$ group in the nitro compound are preferred. The reaction can proceed with less than 3 moles of CO for every $NO_2$ group per mole of nitro compound, however, the amount of co-products will generally increase with the decrease of CO concentration below this preferred level.

The rhodium oxide, which is generally amorphous rhodium dioxide and/or amorphous rhodium sesquioxide, serves as a catalyst and increases the yields of the isocyanates. The amount of rhodium oxide used is a catalytic amount. By catalytic amount is meant an amount sufficient to catalyze the conversion of the nitro compound to isocyanate. Generally, the amount of catalyst should be sufficient to provide about 0.5 gram of rhodium dioxide or sesquioxide per 0.1 mole of nitro compound. At or above these concentrations, using rhodium sesquioxide or dioxide, an organic nitrile compound, and a dinitro compound, large yields of diisocyanates are obtained. Generally, as the concentration of catalyst decreases, the yields of diisocyanates begin to decrease and the yields of monoisocyanates begin to increase.

The reaction is carried out at temperatures ranging from about ambient to about 400° C. Generally the upper range of the temperature should be below that at which polymerization or decomposition of the reaction components occurs to an undesirable extent. Preferred temperatures are from about 100° to about 225° C. The more preferred temperatures are from about 125° to about 190° C. The reaction times will vary, depending to some extent on the temperatures and pressures at which the reaction is carried out. In general, the higher the temperatures and/or pressures, the faster the reaction, and conversely, the lower the temperatures and/or pressures, the slower the reaction rate. Generally the reaction times range from about thirty minutes to about 12 hours.

The process of the present invention works in the absence of a solvent. However, the process works particularly well in the presence of a solvent system which preferably contains at least a small amount of an organic nitrile. Thus, the solvent can be composed entirely of a nitrilic compound, a mixture of nitrilic compounds, or a mixture of a nitrilic compound and nonnitrilic organic solvents or solvent. Examples of other inert organic solvents are the aliphatic or aromatic hydrocarbons such as n-pentane, benzene, toluene, xylene, halogenated aliphatic hydrocarbons such as 1,1,2-trichloro-1,2,2-trifluoroethane, halogenated aromatic hydrocarbons such as monochlorobenzene, dichlorobenzene, trichlorobenzene, and the like.

The amount of solvent used is a solvating amount, i.e., an amount to sufficiently contact the reactants to enable them to coreact to form the isocyanate. The organic nitrile compound can be used as both a solvent and a promoter, i.e. as a yield (isocyanate) enhancer. It has been found that the nitrile compound, when present in even small amounts, has yield enhancing, conversion enhancing, and rate enhancing effects upon the reaction. By yield enhancing effects is meant that the yield of isocyanate particularly the yield of diisocyanate, is increased over that obtained where there is no nitrile compound present. By conversion enhancing effect is meant that the conversion of the nitro compound is increased over that obtained without the nitrile compound. By rate enhancing effect is meant that the rate of the reaction is increased over that of a system without the nitrile compound. In a more preferred embodiment the solvent system used is one comprised of a nitrile compound or a mixture of nitrile compounds. In this embodiment the nitrile compound acts as both a solvent and a yield, rate, and conversion enhancer or promoter. In another embodiment a yield enhancing amount or promoter amount of the nitrile compound can be added to a solvent system comprised of one of the inert organic solvents described above. In this embodiment as little as 1 percent by volume, of nitrile compound can be effective to enhance the rates, yields, and conversions of the reaction. Generally, in this embodiment, the amount of nitrile present, in volume percent of the solvent system, is from about 1 percent to about 99 percent, preferably from about 2 percent to about 50 percent, and more preferably from about 3 percent to about 30 percent. By yield enhancing amount is meant that amount of organic nitrile compound sufficient to increase the yield of the reaction over that of a reaction without an organic nitrile compound. Generally, the proportion of the organic cyano compound to the nitro compound is equivalent to a molar ratio of moles of the organic nitrile compound per mole of organic nitro compound in the range between about 0.05:1 and about 25:1.

This invention is illustrated in the following examples:

EXAMPLE 1

A suitable pressure vessel was charged with 160 ml of acetonitrile, 18.2 grams of 2,4-dinitrotoluene, and 1.00 gram of amorphous rhodium dioxide. The pressure vessel was sealed and purged with nitrogen followed by a carbon monoxide purge. Carbon monoxide was introduced until a pressure of 3,000 p.s.i. was obtained. The pressure vessel was heated to 190° C. The internal pressure was then 4,800 p.s.i. After maintaining the temperature for 2 hours, the pressure vessel was cooled to room temperature. The internal pressure was then 2,950 p.s.i. The pressure vessel was vented and flushed with nitrogen. The reaction mixture was discharged via dip-leg with nitrogen pressure. The reaction mixture was analyzed by Vapor Phase Chromatography. Analysis by Vapor Phase Chromatography indicated a 0.82 percent yield of toluene diisocyanate, a 25.29 percent yield of 5-nitro-o-tolyl isocyanate, a 13.89 percent yield of 3-nitro-p-tolyl isocyanate, and 53.80 percent of dinitrotoluene remaining.

EXAMPLE 2

The general procedure of Example 1 was repeated maintaining the temperature at 190° C. for 5 hours. Analysis of the reaction mixture by Vapor Phase Chromatography indicated trace amounts of toluene diisocyanate, a 22.63 percent yield of 5-nitro-o-tolyl isocyanate, an 11.45 percent yield of 3-nitro-p-tolyl isocyanate and 47.42 percent of dinitrotoluene remain.

EXAMPLE 3

The general procedure of Example 1 was repeated substituting 1 gram of amorphous rhodium sesquioxide ($Rh_2O_3$) for the rhodium dioxide and maintaining the temperature at 190° C. for 5 hours. Analysis of the reaction mixture by Vapor Phase Chromatography indicated a 0.69 percent yield of toluene diisocyanate, a 25.07 percent yield of 5-nitro-o-tolyl isocyanate, a 10.46 percent yield of 3-nitro-p-tolyl isocyanate, a 7.44 percent yield of 5-nitro-o-toluidine, and 56.34 percent of the dinitrotoluene remaining.

EXAMPLE 4

A suitable pressure vessel was charged with 160 ml of benzene, 18.2 grams of 2,4-dinitrotoluene, and 1.00 gram of amorphous rhodium dioxide ($RhO_2$). The pressure vessel was sealed and purged with nitrogen followed by a carbon monoxide purge. Carbon monoxide was introduced until a pressure of 3,000 p.s.i. was obtained. The pressure vessel was heated to 190° C. The internal pressure was then 3,790 p.s.i. After maintaining the temperature for 5 hours, the pressure vessel was cooled to room temperature. The internal pressure was then 2,125 p.s.i. The pressure vessel was vented and flushed with nitrogen. The reaction mixture was discharged via a dip-leg with nitrogen pressure. The reaction mixture was analyzed by Vapor Phase Chromatography. Analysis by Vapor Phase Chromatography indicated a 0.92 percent yield of toluene diisocyanate, a 15.30 percent yield of 5-nitro-o-tolyl isocyanate, a 4.30 percent yield of 3-nitro-p-tolyl isocyanate, and 44.50 percent of the dinitrotoluene remaining.

EXAMPLE 5

The general procedure of Example 4 was repeated except that the catalyst was amorphous rhodium sesquioxide ($Rh_2O_3$), of which 1 gram was used. Analysis of the reaction mixture by Vapor Phase Chromatography indicated a 0.61 percent yield of toluene diisocyanate, an 18.75 percent yield of 5-nitro-o-tolyl isocyanate, a 7.16 percent yield of 3-nitro-p-tolyl isocyanate, and 44.53 percent of the dinitrotoluene remaining.

EXAMPLE 6

The general procedure of Example 4 was repeated except that the catalyst was rhodium sesquioxide and the temperature was maintained at 155° C. for 5 hours. Analysis of the reaction mixture by Vapor Phase Chromatography indicated substantially no toluene diisocyanate, trace amounts of 5-nitro-o-tolyl isocyanate, substantially no 3-nitro-p-tolyl isocyanate, 1.13 percent of 5-nitro-o-toluidine, and 97.12 percent of the dinitrotoluene remaining.

EXAMPLE 7

The general procedure of Example 5 was repeated except that 155 ml of benzene and 5 ml of acetonitrile were used as the solvent system. Analysis of the reaction mixture by Vapor Phase Chromatography indicated a 0.88 percent yield of toluene diisocyanate, a 23.96 percent yield of 5-nitro-o-tolyl isocyanate, an 8.81 percent yield of 3-nitro-p-tolyl isocyanate, and 37.22 percent of the dinitrotoluene remaining.

EXAMPLE 8

The general procedure of Example 5 was repeated except that 150 ml of benzene and 10 ml of acetonitrile were used as the solvent system. Analysis of the reaction mixture by Vapor Phase Chromatography indicated a 0.97 percent yield of toluene diisocyanate, a 24.56 percent yield of 5-nitro-o-tolyl isocyanate, a 7.92 percent yield of 3-nitro-p-tolyl isocyanate, a 1.12 percent yield of 5-nitro-o-toluidine, and 43.68 percent of the dinitrotoluene remaining.

EXAMPLE 9

The general procedure of Example 8 was repeated except that the temperature of 190° C. was maintained for 10 hours. Analysis of the reaction mixture by Vapor Phase Chromatography indicated a 1.08 percent yield of toluene diisocyanate, a 24.0 percent yield of 5-nitro-o-tolyl isocyanate, a 7.83 percent yield of 3-nitro-p-tolyl isocyanate, a 2.26 percent yield of 5-nitro-o-toluidine, and 21.0 percent of the dinitrotoluene remaining.

EXAMPLE 10

The general procedure of Example 4 was repeated substituting 1 gram of $RhBr_3$ for the amorphous rhodium dioxide. Analysis of the reaction mixture by Vapor Phase Chromatography indicated a 0.0006 percent yield of toluene diisocyanate, a 2.45 percent yield of 5-nitro-o-tolyl isocyanate, a 2.00 percent yield of 3-nitro-p-tolyl isocyanate, and 94.62 percent of dinitrotoluene remaining.

EXAMPLE 11

The general procedure of Example 1 was repeated substituting 1.0 gram of $RhI_3$ for the amorphous rhodium dioxide and maintaining the temperature at 190° C. for 5 hours. Analysis of the reaction mixture by Vapor Phase Chromatography indicated substantially no toluene diisocyanate, a 4.09 percent yield of 5-nitro-o-tolyl isocyanate, a 2.05 percent yield of 3-nitro-p-tolyl isocyanate, 2.86 percent of 5-nitro-o-toluidine, and 91.00 percent of the dinitrotoluene remaining.

As can be seen from the foregoing examples, conversion of nitro compounds to the isocyanates is enhanced when the reaction is carried out in the presence of an organic nitrile compound using amorphous rhodium oxide catalyst. However, using an amorphous rhodium oxide catalyst and a solvent system other than one containing an organic nitrile compound, such as benzene, effects conversion of the nitro compound to isocyanate although the yield per period of time is somewhat less than if a solvent system containing a nitrile compound were used.

Thus, one embodiment of the present invention is a process for preparing an aromatic isocyanate which comprises reacting an aromatic nitro compound with carbon monoxide at an elevated temperature and an elevated pressure in the presence of an organic nitrile compound and in the presence of a catalytic amount of substantially amorphous rhodium oxide catalyst.

In a most preferred embodiment the nitro compound is dinitrotoluene and the nitrile compound is acetonitrile and is used and functions as both a solvent and yield enhancer or promoter, the elevated temperatures are from about 125° C. to about 225° C., and the elevated pressures are from about 2,000 p.s.i. to about 5,000 p.s.i.

The elevated temperatures and pressures should be such that the organic nitro compound and carbon monoxide coreact in the presence of the rhodium oxide catalyst to form isocyanates.

By the process of the present invention, compounds containing one or more isocyanate groups can be prepared.

While in the preferred embodiment of the present invention a nitro compound is coreacted with carbon monoxide in the presence of a rhodium oxide catalyst, and an organic nitrile compound, other organic compounds containing at least one nitrogen atom bonded directly to a single carbon atom and to an oxygen or another nitrogen atom may be used in place of the nitro compound to produce isocyanates. Examples of these types of compounds which may be substituted for the nitro compound are the organic nitroso, azo and azoxy compounds.

As previously mentioned, the temperatures and pressures can vary widely and are not critical. They should, however, be such that the nitro compound and carbon monoxide coreact to form isocyanate, but not such, i.e., too high, that polymerization or decomposition of the reaction components occurs to an undesirable extent.

In all of the examples set forth above, yield figures based on analysis by Vapor Phase Chromatography are in area percent. Also in all of these examples, substantially anhydrous conditions were observed.

Claims to the invention follow:

I claim:

1. A process for the preparation of an isocyanate mixture comprising mono- and diisocyanates derivable from an aromatic dinitro compound, said process comprising reacting said dinitro compound with carbon monoxide at an elevated temperature and an elevated pressure in the presence of a rhodium oxide catalyst and a promoter quantity of an alkyl nitrile solvent.

2. A process according to claim 1 wherein said aromatic dinitro compound is dinitrotoluene.

3. A process according to claim 1 wherein said rhodium oxide is rhodium dioxide.

4. A process according to claim 1 wherein said rhodium oxide is rhodium sesquioxide.

5. A process according to claim 4 wherein rhodium sesquioxide is substantially amorphous rhodium sesquioxide.

6. A process according to claim 1 wherein said alkyl nitrile is a lower alkyl nitrile.

7. A process according to claim 6 wherein said lower alkyl nitrile is acetonitrile.

8. A process according to claim 1 wherein said elevated temperature is from about 125° C. to 225° C.

9. A process according to claim 3 wherein said rhodium dioxide is substantially amorphous rhodium dioxide.

10. A process for the preparation of an isocyanate mixture comprising mono- and diisocyanates derivable from an aromatic dinitro compound, said process comprising reacting said dinitro compound with carbon monoxide at an elevated temperature and an elevated pressure in the presence of an amorphous rhodium oxide catalyst and a promoter quantity of an alkyl nitrile solvent.

11. A process according to claim 10 wherein said aromatic dinitro compound is dinitrotoluene.

12. A process according to claim 10 wherein said amorphous rhodium oxide catalyst is amorphous rhodium dioxide.

13. A process according to claim 10 wherein said amorphous rhodium oxide catalyst is amorphous rhodium sesquioxide.

14. A process according to claim 10 wherein said alkyl nitrile is acetonitrile.

15. A process according to claim 10 wherein said elevated temperature is from about 125° C. to 225° C.

* * * * *